US006815416B2

(12) United States Patent
Carney et al.

(10) Patent No.: US 6,815,416 B2
(45) Date of Patent: Nov. 9, 2004

(54) STIMULATION OF CARTILAGE GROWTH WITH AGONISTS OF THE NON-PROTEOLYTICALLY ACTIVATED THROMBIN RECEPTOR

(75) Inventors: Darrell H. Carney, Dickinson, TX (US); Roger S. Crowther, League City, TX (US); Janet Stiernberg, Paris, TX (US); John Bergmann, Galveston, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 18 days.

(21) Appl. No.: 09/909,348

(22) Filed: Jul. 19, 2001

(65) Prior Publication Data

US 2002/0042373 A1 Apr. 11, 2002

Related U.S. Application Data

(60) Provisional application No. 60/219,800, filed on Jul. 20, 2000.

(51) Int. Cl.$^7$ ............................................... A01N 37/18
(52) U.S. Cl. ................................. 514/2; 514/2; 514/13; 424/422; 424/94.64; 424/78.08; 530/350; 530/399; 530/326
(58) Field of Search ...................... 514/2, 13; 424/422, 424/94.64, 78.08; 530/350, 326, 399

(56) References Cited

U.S. PATENT DOCUMENTS

| 5,352,664 A | 10/1994 | Carney et al. ................. 514/13 |
| 5,500,412 A | 3/1996 | Carney et al. ................. 514/13 |
| 5,876,452 A | 3/1999 | Athanasiou et al. ........... 623/16 |
| 6,001,352 A | 12/1999 | Boyan et al. ............... 424/93.7 |

FOREIGN PATENT DOCUMENTS

WO  WO 88/03151  5/1988

OTHER PUBLICATIONS

O'Connor, W.J., et al., "The Use of Growth Factors in Cartilage Repair," *Orthopedic Clinics of North America*, 31(3): 399–409 (2000).
Frenkel, S.R., et al., "Transforming Growth Factor Beta Superfamily Members: Role in Cartilage Modeling," *Plastic and Reconstructive Surgery*, 105(3): 980–990 (2000).
Sellers, R.S., et al., "Repair of Articular Cartilage Defects One Year After Treatment with Recombinant Human Bone Morphogenetic Protein–2 (rhBMP–2)," *J. of Bone & Joint Surgery*, 82(2): 151–160 (2000).
Sanyal, A., et al., "Initial Evidence for the Involvement of Bone Morphogenetic Protein–2 Early during Periosteal Chondrogenesis," *J. of Orthopaedic Research*, 17(6): 926–934 (1999).

Louwerse, R.T., et al., "Use of Recombinant Human Osteogenic Protein–1 for the Repair of Subchondral Defects in Articular Cartilage in Goats," *J. of Biomedical Materials Res.*, 49(4): 506–516 (2000).
Nixon, A.J., et al., "Enhanced Repair of Extensive Articular Defects by Insulin–Like Growth Factor–I–Laden Fibrin Composites," *J. of Orthopaedic Res.*, 17: 475–487 (1999).
Fujimoto, E., et al., "Beneficial Effect of Basic Fibroblast Growth Factor on the Repair of Full–Thickness Defects in Rabbit Articular Cartilage," *Archives of Orthopaedic and Trauma Surgery*, 119(3–4): 139–145 (1999).
Koepp, H.E., et al., "Osteogenic Protein–1 (OP–1) Blocks Cartilage Damage Caused by Fibronectin Fragments and Promotes Repair by Enhancing Proteoglycan Synthesis," *Inflammation Res.*, 48(4): 199–204 (1999).
Hogervorst, T., et al., "The Effect of a TCP–Collagen Implant on the Healing of Articular Cartilage Defects in the Rabbit Knee Joint," *J. of Applied Biomaterials*, 3: 251–258 (1992).
Reddi, A.H., "Cartilage–Derived Morphogenetic Proteins and Cartilage Morphogenesis," *Microscopy Res. & Technique*, 43(2): 131–136 (1998).
Stiernberg, J., et al., "The Role of Thrombin and Thrombin Receptor Activating Peptide (TRAP–508) in Initiation of Tissue Repair," *Thrombosis and Haemostasis*, 70(1): 158–162 (1993).
Carney, D.H., et al., "Enhancement of Incisional Wound Healing and Neovascularization in Normal Rats by Thrombin and Synthetic Thrombin Receptor–Activating Peptides," *J. Clin. Invest.* 89: 1469–1477 (1992).
Carney, D.H., et al., "Role of High–Affinity Thrombin Receptors in Postclotting Cellular Effects of Thrombin," *Seminars in Thrombosis and Hemostasis*, 18(1): 91–102 (1992).
Stiernberg, J., et al., "Acceleration of Full–Thickness Wound Healing in Normal Rats by the Synthetic Thrombin Peptide, TP508," *Wound Repair and Regeneration*, 8(3): 204–215 (2000).
Sower, L.E., et al., "Thrombin Peptide, TP508, Induces Differential Gene Expression in Fibroblasts Through a Nonproteolytic Activation Pathway," *Experimental Cell Res.*, 247: 422–431 (1999).

(List continued on next page.)

*Primary Examiner*—Karen Cochrane Carlson
*Assistant Examiner*—Hope A. Robinson
(74) *Attorney, Agent, or Firm*—Hamilton, Brook, Smith & Reynolds, P.C.

(57) ABSTRACT

Disclosed is a method of stimulating cartilage growth, repair or regeneration at a site in a subject in need of such growth, repair or regeneration. The method comprises the step of administering a therapeutically effective amount of an agonist of the non-proteolytically activated thrombin receptor to the site.

Also disclosed is a method of stimulating the proliferation and expansion of chrondrocytes in vitro. The method comprises culturing chrondrocytes in the presence of a stimulating amount of an NPAR agonist.

21 Claims, No Drawings

OTHER PUBLICATIONS

Glenn, K.C., et al., "Synthetic Peptides Bind to High–Affinity Thrombin Receptors and Modulate Thrombin Mitogenesis," *The J. of Peptide Application, Synthesis and Analysis*, 1(2): 65–73 (1988).

Carney, D.H., "Postclotting Cellular Effects of Thrombin Mediated by Interaction With High–Affinity Thrombin Receptors," in Thrombin: Structure and Function, ed. Lawrence J. Berliner. Plenum Press, New York, 351–396, 1992.

Nishida, Y., et al., "Osteogenic proten–1 promotes the syntehsis and retention of extracellular matrix wihing bovine articular cartilage and chondrocyte cultures," *Osteoarthritis and Cartilage*, 8: 127–136 (2000).

Crowther, R.S., et al., "Thrombin Peptide TP508 Significantly Accelerates Repair of Fresh Fractures," *Distributed at Texas Mineralized Tissue Society*, Austin, Texas. Aug. 1998.

Simmons, D.J., et al., "Acceleration of Rat Femoral Fracture Healing by a Synthetic Thrombin Peptide," *Calcium Metabolism: Comparative Endocrinology.* Proc Satellite Meeting, San Francisco, CA. Nov. 30, 1998. (Eds. C Dacke, J Danks, G Glik and C Gay). BioScientifica Ltd. Bradley Stoke, Bristol, UK. 1999.

Yang et al., "Accelerated Repair of Segmental Defects by a Synthetic Thrombin Peptide," Handout that was distributed at the Texas Mineralized Tissue Society Meeting, Sep., 1999.

Kurray Co LTD. (Accession No. AAW83414, Dec. 2, 1998).

SEQUENCE LISTING

<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: peptide fragment of thrombin

<400> SEQUENCE: 1

Cys Glu Gly Asp Ser Gly Gly Pro Phe Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: peptide fragment of thrombin
<220> FEATURE:
<221> NAME/KEY: VARIANT
<222> LOCATION: (2)...(2)
<223> OTHER INFORMATION: Xaa = Glu or Gln
<220> FEATURE:
<221> NAME/KEY: VARIANT
<222> LOCATION: (9)...(9)
<223> OTHER INFORMATION: Xaa = Phe, Met, Leu, His or Val

<400> SEQUENCE: 2

Cys Xaa Gly Asp Ser Gly Gly Pro Xaa Val
1               5                   10

<210> SEQ ID NO 3
<211> LENGTH: 4
<212> TYPE: PRT
<213> ORGANISM: Artificial Sequence
<220> FEATURE:
<223> OTHER INFORMATION: peptide fragment of thrombin

<400> SEQUENCE: 3

Arg Gly Asp Ala
1

<210> SEQ ID NO 4
<211> LENGTH: 14

-continued

```
<212> TYPE: PRT
<213> ORGANISM: Artificial Sequence
<220> FEATURE:
<223> OTHER INFORMATION: peptide fragment of thrombin
<220> FEATURE:
<221> NAME/KEY: VARIANT
<222> LOCATION: (6)...(6)
<223> OTHER INFORMATION: Xaa = Glu or Gln
<220> FEATURE:
<221> NAME/KEY: VARIANT
<222> LOCATION: (13)...(13)
<223> OTHER INFORMATION: Xaa = Phe, Met, Leu, His or Val

<400> SEQUENCE: 4

Arg Gly Asp Ala Cys Xaa Gly Asp Ser Gly Gly Pro Xaa Val
1               5                   10

<210> SEQ ID NO 5
<211> LENGTH: 23
<212> TYPE: PRT
<213> ORGANISM: Artificial Sequence
<220> FEATURE:
<223> OTHER INFORMATION: peptide fragment of thrombin

<400> SEQUENCE: 5

Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 6
<211> LENGTH: 23
<212> TYPE: PRT
<213> ORGANISM: Artificial Sequence
<220> FEATURE:
<223> OTHER INFORMATION: peptide fragment of thrombin
<220> FEATURE:
<221> NAME/KEY: AMIDATION at C-terminus
<222> LOCATION: (23)...(23)
<223> OTHER INFORMATION: Valine is Amidated

<400> SEQUENCE: 6

Ala Gly Tyr Lys Pro Asp Glu Gly Lys Arg Gly Asp Ala Cys Glu Gly
1               5                   10                  15

Asp Ser Gly Gly Pro Phe Val
            20
```

STIMULATION OF CARTILAGE GROWTH WITH AGONISTS OF THE NON-PROTEOLYTICALLY ACTIVATED THROMBIN RECEPTOR

RELATED APPLICATIONS

This application claims the benefit of U.S. Provisional Application No. 60/219,800, filed Jul. 20, 2000, the entire teachings of which are incorporated herein by reference.

GOVERNMENT SUPPORT

The invention was supported, in whole or in part, by grant 1 R43 AR46343-01 from the National Institutes of Health/National Institute of Arthritis and Muscoskeletal and Skin Diseases. The Government has certain rights in the invention.

BACKGROUND OF THE INVENTION

Unlike most tissues, cartilage does not self-repair following injury. Cartilage is an avascular tissue made up largely of cartilage specific cells, the chondrocytes, special types of collagen, and proteoglycans. The inability of cartilage to self-repair after injury, disease, or surgery is a major limiting factor in rehabilitation of degrading joint surfaces and injury to meniscal cartilage. Osteoarthritis, the major degenerative disease of weight bearing joint surfaces, is caused by eroding or damaged cartilage surfaces and is present in approximately 25% of the over 50-year-old population. In the US more than 20 million people suffer from osteoarthritis, with annual healthcare costs of more than $8.6 billion. In addition, the cost for cartilage repair from acute joint injury (meniscal lesions, patellar surface damage and chondromalacia) exceeds $1 billion annually. Therefore, new therapeutic approaches are needed to heal lesions of cartilage caused by degeneration or acute trauma.

SUMMARY OF THE INVENTION

It has now been found that chondrocytes isolated from articular cartilage respond to compounds which activate the non-proteolytic thrombin cell surface receptor (hereinafter "NPAR"). For example, chondrocytes express approximately 233,000 thrombin binding sites per cell with apparent affinities of approximately 0.1 nM (3000 sites) and 27 nM (230,000 sites) (Example 1). In addition, the compound TP508, an agonist of the non-proteolytic thrombin receptor, stimulates proliferation of bovine chondrocytes in culture in the presence of thrombin as a co-mitogen (Example 2A) and stimulates by itself the proliferation of rat chondrocytes cultured in three dimensional matrix culture (Example 3A). This same TP508 compound also stimulates proteoglycan synthesis as measured by the incorporation of $^{35}S$ sulfate in both bovine chondrocytes (Example 2B) and 3-dimensional cultures of rat chondrocytes (Example 3B). These in vitro experiments demonstrate that NPAR agonists can stimulate proliferation and matrix production in chondrocytes isolated from articular cartilage. Additional in vivo experiments demonstrate that delivering TP508 in a sustained release formulation to rabbit trochlear grove cartilage defects which extend into the subchondral bone results in repair of the cartilage defect, including repair of subchondral bone, restoration of a normal cartilage surface and integration of the newly formed cartilage with uninjured cartilage outside of the defect area (Example 5).

Based on the results reported in the prior paragraph, novel methods of stimulating chondrocyte growth in vivo and cartilage repair in a subject and novel delivery methods for delivering pharmaceutical compositions to articular defects to aid in surface repair and to prevent articular degradation are disclosed herein.

The present invention is a method of stimulating cartilage growth, regeneration or repair at a site in a subject where cartilage growth, repair or regeneration is needed. The method comprises the step of administering a therapeutically effective amount of an agonist of the non-proteolytically activated thrombin receptor to the site of injury.

Another embodiment of the present invention is a method of stimulating the proliferation and expansion of chrondrocytes in vitro. The method comprises culturing chrondrocytes in the presence of a stimulating amount of an NPAR agonist.

DETAILED DESCRIPTION OF THE INVENTION

Sites in need of cartilage growth, repair or regeneration are found in subjects with osteoarthritis. Osteoarthritis or degenerative joint disease is a slowly progressive, irreversible, often monoarticular disease characterized by pain and loss of function. The underlying cause of the pain and debilitation is the cartilage degradation that is one of the major symptoms of the disease. Hyaline cartilage is a flexible tissue that covers the ends of bones and lies between joints such as the knee. It is also found in between the bones along the spine. Cartilage is smooth, allowing stable, flexible movement with minimal friction, but is also resistant to compression and able to distribute applied loads. As osteoarthritis progresses, surfaces of cartilage and exposed underlying bone become irregular. Instead of gliding smoothly, boney joint surfaces rub against each other, resulting in stiffness and pain. Regeneration of damaged cartilage and the growth of new cartilage at these arthritic sites would relieve the pain and restore the loss of function associated with osteoarthritis.

Cartilage damage can also occur from trauma resulting from injury or surgery. Sports injuries are a common cause of cartilage damage, particularly to joints such as the knee. Traumatic injury to cartilage can result in the same type of functional impairment. Therefore, sites in a subject with cartilage that has been damaged by trauma or disease are in need of treatment to restore or promote the growth of cartilage.

Applicants have discovered that compounds which stimulate or activate the non-proteolytically activated thrombin receptor (hereinafter "NPAR") can stimulate chondrocytes to proliferate. Chondrocytes are cells which make up about 1% of the volume of cartilage and which replace degraded matrix molecules to maintain the correct volume and mechanical properties of the tissue. Applicants have also found that compounds which stimulate or activate NPAR stimulate proteoglycan synthesis in chondrocytes. Proteoglycan is a major cartilage component. Based on these results, Applicants delivered the NPAR agonist TP508, prepared in a sustained release formulation, to defects in rabbit trochlear grove cartilage and discovered that the peptide stimulated repair of the defect that included formation of new cartilage with a normal cartilage surface. The peptide also stimulated layering and integration of this new cartilage into adjacent, uninjured cartilage and restoration of the subchondral bone. It is concluded that NPAR agonists can induce cartilage growth and repair when administered to sites needing cartilage growth and/or repair.

Compounds which stimulate or activate NPAR are said to be NPAR agonists. NPAR is a high-affinity thrombin receptor present on the surface of most cells. NPAR is largely responsible for high-affinity binding of thrombin, proteolytically inactivated thrombin, and thrombin derived peptides to cells. NPAR agonists and antagonists can compete for the affinity binding with thrombin to cells (see, e.g., Glenn et al., *J. Peptide Research* 1:65 (1988)). NPAR appears to mediate a number of cellular signals that are initiated by thrombin independent of its proteolytic activity. An example of one such signal is the upregulation of annexin V and other molecules identified by subtractive hybridization (see Sower, et. al., *Experimental Cell Research* 247:422 (1999)). NPAR is therefore characterized by its high affinity interaction with thrombin at cell surfaces and its activation by proteolytically inactive derivatives of thrombin and thrombin derived peptide agonists as described below. NPAR activation can be assayed based on the ability of its agonists, to stimulate cell proliferation when added to fibroblasts in the presence of submitogenic concentrations of thrombin or molecules that activate protein kinase C as disclosed in U.S. Pat. Nos. 5,352,664 and 5,500,412.

NPAR is to be distinguished from other thrombin binding proteins and the cloned family of proteolytically-activated receptors for thrombin, including the receptors PAR1, PAR2, PAR3 and PAR4. PAR1 possesses a specific thrombin cleavage site that allows thrombin cleavage to expose a new amino-terminus domain that acts as a tethered ligand folding back onto itself inducing its activation (see, Vu, et al., *Cell*. 64:1057 (1991)). PAR2 has a similar mechanism for activation, but is principally activated by trypsin-like enzymes (see, Zhong, et al, *J. Biol. Chem*. 267:16975 (1992)). PAR3 also has a similar mechanism of activation and appears to function as a second thrombin receptor in platelets (see, Ishihara, et al., *Nature*. 386:502 (1997)). PAR4 has been detected in mouse megakaryocytes and studies suggest that it also functions in human platelets (see, Kahn, et al., *Nature* 394:690 (1998)). In contrast with these PAR receptors, activation of NPAR requires no proteolytic cleavage.

Several lines of evidence indicate that NPAR is distinct from PAR receptors: (1) a population of cells has been isolated that express fully functional PAR1 receptors, but are non-responsive to thrombin due to a defect in the NPAR signal transduction pathway (see, Kim, et al., *J. Cell. Physiol*. 160:573 (1994)); (2) neutrophils bind $^{125}$I thrombin with high affinity and their chemotaxis is stimulated by proteolytically inactivated thrombin or NPAR agonists (see, Ramakrishnan and Carney, *Mol. Biol. Cell* 4. 1993 (1993)), yet they do not express PAR1 (see Jenkins, et al., *J. Cell Sci*. 108:3059 (1995)); (3) IIC9 fibroblasts over-express PAR1, but do not bind thrombin with high affinity (see, Kim, D. Ph.D. Dissertation. The University of Texas Medical Branch at Galveston, 1995; and Low, et al., "Cancer Cells 3/Growth Factors and Transformation", Cold Spring Harbor Laboratory, New York); and (4) NPAR agonists have distinct effects on gene expression from those of the PAR receptor agonist peptides (see, Sower, et. al., *Experimental Cell Research* 247: 422 (1999).

One example of an NPAR agonist is a thrombin peptide derivative and physiologically functional equivalents, i.e., a polypeptide with no more than about fifty amino acids, preferably no more than about thirty amino acids and having sufficient homology to the fragment of human thrombin corresponding to prothrombin amino acids 508–530 (SEQ ID NO: 5) that the polypeptide activates NPAR. The thrombin peptide derivatives described herein preferably have between about 12 and 23 amino acids, more preferably between about 19 and 23 amino acids. One example of a thrombin peptide derivative comprises a moiety represented by Structural Formula (I):

Asp-Ala-R    (I)

R is a serine esterase conserved domain. Serine esterases, e.g., trypsin, thrombin, chymotrypsin and the like, have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability.

In one embodiment, the serine esterase conserved sequence has the amino acid sequence of SEQ ID NO: 1 (Cys-Glu-Gly-Asp-Ser-Gly-Gly-Pro-Phe-Val) or a C-terminal truncated fragment of a polypeptide having the amino acid sequence of SEQ ID NO: 1. It is understood, however, that zero, one, two or three amino acids in the serine esterase conserved sequence can differ from the corresponding amino acid in SEQ ID NO: 1. Preferably, the amino acids in the serine esterase conserved sequence which differ from the corresponding amino acid in SEQ ID NO: 1 are conservative substitutions, and are more preferably highly conservative substitutions. A "C-terminal truncated fragment" refers to a fragment remaining after removing an amino acid or block of amino acids from the C-terminus, said fragment having at least six and more preferably at least nine amino acids.

More preferably, the serine esterase conserved sequence has the amino acid sequence of SEQ ID NO: 2 (Cys-$X_1$-Gly-Asp-Ser-Gly-Gly-Pro-$X_2$-Val; $X_1$ is Glu or Gln and $X_2$ is Phe, Met, Leu, His or Val) or a C-terminal truncated fragment thereof having at least six amino acids, preferably at least nine amino acids.

In a preferred embodiment, the thrombin peptide derivative comprises a serine esterase conserved sequence and a polypeptide having a more specific thrombin amino acid sequence In a preferred embodiment, the thrombin peptide derivative comprises a serine esterase conserved sequence and a polypeptide having a more specific thrombin amino Arg-Gly-Asp-Ala (SEQ ID NO: 3). One example of a thrombin peptide derivative of this type comprises Arg-Gly-Asp-Ala-Cys-$X_1$-Gly-Asp-Ser-Gly-Gly-Pro-$X_2$-Val (SEQ ID NO: 4). $X_1$ and $X_2$ are as defined above. When the thrombin peptide derivative comprises SEQ ID NO: 4, it preferably has the amino acid sequence of SEQ ID NO: 5 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val) or an N-terminal truncated fragment thereof, provided that zero, one, two or three amino acids at positions 1–9 in the thrombin peptide derivative differ from the amino acid at the corresponding position of SEQ ID NO: 5. Preferably, the amino acids in the thrombin peptide derivative which differ from the corresponding amino acid in SEQ ID NO: 5 are conservative substitutions, and are more preferably highly conservative substitutions. An "N-terminal truncated fragment" refers to a fragment remaining after removing an amino acid or block of amino acids from the N-terminus, preferably a block of no more than six amino acids, more preferably a block of no more than three amino acids.

TP508 is an example of a thrombin peptide derivative and has the amino acid sequence of SEQ ID NO: 5. A physiologically functional equivalent of SEQ ID NO: 5 is SEQ ID NO: 6 which has the identical amino acid sequence of SEQ ID NO: 5 and also contains a C-terminal amide.

A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in the their side chains differs by no more than one. Amino acids with phenyl or substituted phenyl groups in their side chains are considered to have about the same size and shape. Listed below are five groups of amino acids. Replacing an amino acid in a polypeptide with another amino acid from the same group results in a conservative substitution:

Group I: glycine, alanine, valine, leucine, isoleucine, serine, threonine, cysteine, and non-naturally occurring amino acids with C1–C4 aliphatic or C1–C4 hydroxyl substituted aliphatic side chains (straight chained or monobranched).

Group II: glutamic acid, aspartic acid and non-naturally occurring amino acids with carboxylic acid substituted C1–C4 aliphatic side chains (unbranched or one branch point).

Group III: Lysine, ornithine, arginine and non-naturally occurring amino acids with amine or guanidino substituted C1–C4 aliphatic side chains (unbranched or one branch point).

Group IV: glutamine, asparagine and non-naturally occurring amino acids with amide, substituted C1–C4 aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Example of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

Other NPAR agonists include small organic molecules which bind and activate NPAR. Agonists of this type can be conveniently identified with high through-put screening, e.g., with assays that assess the ability of molecules to stimulate cell proliferation when added to fibroblasts in the presence of submitogenic concentrations of thrombin or molecules that activate protein kinase C or with assays that assess the ability of these molecules to compete with $^{125}$I-thrombin to cells with surface NPAR receptors, as disclosed in Glenn et al., supra, U.S. Pat. Nos. 5,352,664 and 5,500, 412. The entire teachings for Glenn et al., and U.S. Pat. Nos. 5,352,664 and 5,500,412 are incorporated herein by reference.

The term "NPAR agonist" also includes compounds and combinations of compounds known to activate NPAR. Examples are disclosed in U.S. Pat. Nos. 5,352,664 and 5,500,412 and include thrombin and DIP-alpha-thrombin.

NPAR agonists used in the method of the present invention are typically administered as one component in a pharmaceutical composition to the site in need of cartilage growth, repair or regeneration. Administering to the site in need of treatment means that the pharmaceutical composition containing the NPAR agonist is administered in sufficient proximity to the site in need of treatment so that cartilage growth or cartilage regeneration occurs at the site (e.g., a greater amount of cartilage growth or better quality of cartilage growth in the presence of the NPAR agonist than in its absence).

In one means of administration, the pharmaceutical composition is a solution comprising the NPAR agonist and a suitable carrier. The solution is applied directly to or in near proximity to the site in need of treatment. Administration of the solution can be conveniently accomplished, for example, intraarticularly by syringe, in close proximity to the damaged tissue by syringe or through a surgical opening. Standard pharmaceutical formulation techniques may be employed such as those described in Remington's Pharmaceutical Sciences, Mack Publishing Company, Easton, Pa. Suitable pharmaceutical carriers for include, for example, physiological saline, bacteriostatic saline (saline containing about 0.9% mg/ml benzyl alcohol), phosphate-buffered saline, Hank's solution, Ringer's-lactate and the like.

In another means of administration, the pharmaceutical composition comprises the NPAR agonist and an implantable biocompatible carrier. A biocompatible carrier should be non-toxic, non-inflammatory, non-immunogenic and devoid of other undesired reactions at the implantation site. Suitable carriers also provide for release of the active ingredient and preferably for a slow, sustained release over time at the implantation site.

A number of synthetic biodegradable polymers can serve as carriers with sustained release characteristics. Examples of these polymers include poly α-hydroxy esters such as polylactic acid/polyglycolic acid copolymers and polyanhydrides.

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., Adv. Drug Deliv. Rev. 28:5 (1997), the entire teachings of which are incorporated herein by reference). The incorporation of poly(ethylene glycol) into the polymer blend allows further attenuation of the release profile of the active ingredient (see Cleek et al., J. Control Release 48:259 (1997), the entire teachings of which are incorporated herein by reference). Suitable implantable PLGA polymers for use as carriers for cartilage growth factors are described in U.S. Pat. Nos. 6,013,853, 5,607,474 and 5,876,452, the entire teachings of which are incorporated herein by reference.

Polyanhydrides, shown in Structural Formula (II), have well defined degradation and release characteristics that can be controlled by including varying amounts of hydrophobic or hydrophilic monomers such as sebacic acid and 1,3-bis (p-carboxyphenoxy)propane (see Leong et al., J. Biomed. Mater. Res. 19:941 (1985), the entire teachings of which are incorporated herein by reference). To improve mechanical strength, anhydrides are often copolymerized with imides to form polyanhydride-co-imides. Examples of polyanhydride-co-imides that are suitable for orthopaedic applications are poly(trimellitylimido-glycine-co-1,6-bis(carboxyphenoxy) hexane and pyromellityimidoalanine:1,6-bis(p-carboxyphenoxy)hexane copolymers.

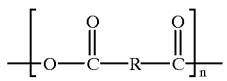

(II)

The pharmaceutical compositions can be shaped as desired in anticipation of surgery or shaped by the physician or technician during surgery. It is preferred to shape the matrix to span a tissue defect and to take the desired form of the new tissue. In the case of cartilage repair of large defects, it is desirable to use dimensions that span the defect. After implantation, the material is slowly absorbed by the body and is replaced by cartilage in the shape of or very nearly the shape of the implant.

In one aspect, the carrier is a porous matrix into which progenitor cells may migrate. Cells can often attach to such porous matrices, which can then serve as a scaffolding for tissue growth and thereby accelerate the rate of bone growth. Chondrocytes can be applied to such matrices prior to implant to further accelerate healing. Collagen or a collagen gel is an example of a suitable porous matrix.

In another aspect, the carrier is a viscous solution or gel that is injectable intraarticuarly or at the site in need of treatment. Hyaluronic acid is an example of a carrier of this type. Hyaluronic acid products are commercially available and include ORTHOVISC developed by Anika, SYNVISC, developed by Biomatrix, HYALGAN, developed by Fidia and ARTZ, developed by Seikagaku. Pluronic gel is another example of this type of carrier. Pluronic gels are nontxoic block copolymers of ethylene oxide and propylene oxide. They exhibit thermosetting properties that allow them to exist as viscous liquids at room temperatures, but as gels at body temperatures. Injectable compositions can be applied directly to the site in need of treatment without the need for invasive surgery. Polymers of poly(ethylene oxide) and copolymers of ethylene and propylene oxide are also suitable as injectable matrices (see Cao et al., *J. Biomater. Sci* 9:475 (1998) and Sims et al., *Plast Reconstr.Surg.* 98:843 (196), the entire teachings of which are incorporated herein by reference).

A "therapeutically effective amount" is the quantity of NPAR agonist (or chondrocytes) which results in greater cartilage growth or repair in the presence of the NPAR agonist than in its absence. Alternatively or addition, a "therapeutically effective amount" is the quantity of NPAR agonist (or chondrocytes) which results in alleviation of the pain and/or lack of function associated with the cartilage damage. Typically, the agonist (or chondrocytes) is administered for a sufficient period of time to achieve the desired therapeutic or effect. The amount administered will depend on the amount of cartilage growth that is desired, the health, size, weight, age and sex of the subject and the release characteristics of the pharmaceutical formulation. Typically, between about 0.1 $\mu$g per day and about 1 mg per day of NPAR agonist (preferably between about 5 $\mu$g per day and about 100 $\mu$g per day) is administered by continuous release or by direct application to the site in need of carilage growth or repair.

A "subject" is preferably a human, but can also be an animal in need of treatment, e.g., companion animals (e.g., dogs, cats, and the like), farm animals (e.g., cows, pigs, horses and the like) and laboratory animals (e.g., rats, mice, guinea pigs and the like).

NPAR agonists can be used to accelerate the growth or to maintain the functionality of isolated chondrocytes. In one embodiment, NPAR agonists can be added to tissue culture medium to stimulate proliferation and provide for more rapid proliferation and/or to prevent apoptotic death or senescence of cells often encountered when primary cell isolates are place in culture. In another embodiment, because the NPAR agonists appear to stimulate matrix production, such NPAR agonists could be used to maintain the differentiated functionality of chondrocytes in culture. NPAR agonists can be used alone in standard defined tissue culture medium or as a supplement to tissue culture medium containing serum or other growth factor to provide additive or synergistic effects or the in vitro production or maintenance of chondrocytes. A sufficient quantity of the NPAR agonist is added to the culture to provide more rapid growth or to maintain greater functionality of the chondrocytes than in the absence of the agonist, i.e., a "stimulatory amount". Typically, between about 0.1 $\mu$g/ml and about 100 $\mu$g/ml of NPAR agonist is used.

Chondrocytes cultured in the presence of an NPAR agonists can also be used to treat cartilage damage by administering a therapeutically effective amount of the chondrocytes to the site in need of treatment. With respect to chondrocytes, "therapeutically effective" also means which results in greater cartilage growth or repair with the treatment than in its absence. The administration of chondrocytes to treat cartilage damage is described in U.S. Pat. No. 4,846,835, the entire teachings of which are incorporated herein by reference.

Thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48–267; and Barany and Merrifield, in *The Peptides*, E. Gross and J. Meienhofer, Eds., Academic Press, New York, 1980, pp. 3–285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these six articles are incorporated herein by reference in their entirety.

The invention is illustrated by the following examples which are not intended to be limiting in any way.

EXEMPLIFICATION

Details of Experiments

Chondrocytes are the primary cell type found in cartilage. In cartilage these cells are normally quiescent, or non-proliferative, and have relatively low metabolic rates. Following injury to cartilage these cells do not readily participate in the repair process. Due to the avascular nature of cartilage, these cells presumably would not see thrombin as an initiator of the repair process.

The following examples demonstrate that chondrocytes have thrombin receptors and that compounds that activate NPAR stimulate chondrocyte proliferation and synthesis of matrix proteoglycans.

EXAMPLE 1

Thrombin Binding to Rat Chondrocytes

Primary cultures of rat articular chondrocytes were isolated and prepared for in vitro analysis using established methods (see Kuettner, K E., et.al., J. Cell Biology 93: 743–750, 1982). Briefly, cartilage pieces were dissected from the shoulder of rats and the pieces were digested with trypsin for one hour and with collagenase for three hours in tissue culture medium (DMEM) at 37 C with stirring. The cells were plated in flasks at high density (50,000 cells/cm sq.) and were culture in DMEM containing antibiotics an ascorbic acid at 37° C. in an atmosphere of 5% $CO_2$.

The specific binding of $^{125}I$ thrombin to chondrocytes was carried out using established thrombin receptor binding assays as disclosed in U.S. Pat. No. 5,352,664 and Carney, D H and Cunningham, D D, Cell 15:1341–1349, 1978. Briefly, highly purified human thrombin was iodinated and added to cultures of chondrocytes with or without unlabeled thrombin to correct for nonspecific binding. By incubating cells with different concentrations of labeled thrombin and measuring the amount of thrombin bound to cells and the amount of free thrombin in the medium it is possible to estimate the number of receptors per cell and the affinity of thrombin for that binding site.

Scatchard analysis of the labeled thrombin binding from three separate experiments suggest that rat chondrocytes express an average of 3000 very high affinity binding sites (100 pM affinity) and 230,000 high affinity sites (27 nM).

EXAMPLE 2A
NPAR Agonist Stimulation of Bovine Chondrocyte Proliferation

Primary cultures of bovine chondrocytes were prepared using the procedure described for rat chondrocytes in Example 1. The cultures were subcultured into 24 well plastic dishes at a low density and placed in 1% serum. Addition of the NPAR agonist TP508 to these cultures at concentrations of 1.0 or 10 μg/ml by itself did not stimulate cell proliferation. In contrast, addition of these concentrations of TP508 together with a small amount of thrombin co-mitogen, resulted in a small, but significant ($p<0.05$) increase in cell number relative to that seen in thrombin alone after three days in culture.

EXAMPLE 2B
NPAR Agonist Stimulation of Bovine Chondrocyte Proteoglycan Synthesis To determine the effect of NPAR agonists on proteoglycan synthesis, bovine chondrocytes were seeded into 96 well plates at a density of 2×105 cells per well and cultured in DMEM with 10% fetal calf serum. After establishment of these multi-layer cultures, the medium was replaced daily with DMEM containing 1% serum with indicated concentrations of TP508 from 1 to 100 μg per ml (Table 1). After 6 days in culture with daily changes of culture medium with or without TP508, $^{35}S$ sulfate was added to the medium and incubation continued for an additional 24 hours. As shown in Table 1, treatment with high concentrations of TP508 (100 μg per ml) increased $^{35}S$ sulfate incorporation relative to untreated cells by more than 10-fold.

TABLE 1

Effect of the NPAR agonist TP508 on $^{35}S$ sulfate incorporation in bovine chondrocyte cultures.

| Treatment | Mean CPM 1% Serum | Std. Dev of Mean |
|---|---|---|
| Control | 4975 | 3552 |
| TP508 (1 μg/ml) | 4701 | 2692 |
| TP508 (10 μg/ml) | 6960 | 3265 |
| TP508 (100 μg/ml) | 81946 | 13783 |

EXAMPLE 3A
A NPAR Agonist Stimulation of Proliferation Synthesis in Cultured Rat Articular Chondrocytes Rat articular chondrocytes were isolated from slices of rat articualar shoulder cartilage utilizing trypsin and collagenase digestions as described in Example 1. Preparations of chondrocyte "3-dimensional" alginate bead cultures were established using established techniques as described by Guo et. al., (Conn. Tiss. Res. 19:277–297, 1998). Following removal of cells from tissue culture flasks with trypsin, the cells were suspended in an alginate gel (1.2% w/v) and slowly expressed through a 22 gauge needle in a dropwise fashion into 102 mM $CaCl_2$. As the drops contact the $CaCl_2$ there is a nearly instantaneous polymerization of the alginate to create a gel bead. The beads were then washed three times in DMEM culture medium and transferred to 35 mm dishes and maintained in culture at 37 C in a 5% CO2 atmosphere by feeding with culture medium every two days.

The effect of NPAR agonist TP508 on chondrocyte cell proliferation after three days in 3-dimensional alginate culture was determined by removing beads from 35 mm dishes, washing them with 0.9% saline, and dissolving the alginate beads by adding 1 ml of 55 mM sodium citrate, 0.15 M NaCl at 37° C. for 10 minutes. Cell number was determined by diluting the 1 ml of dissolved beads 1:10 with phosphate buffered saline (PBS) and counting the cells with a Z-series Coulter Counter. As shown in Table 2, TP508 by itself stimulated proliferation of chondrocytes in 3 dimensional culture.

TABLE 2

Effect of the NPAR agonist TP508 on Proliferation of Rat Chondrocytes in 3-D Bead Culture.

| Treatment | Cells/bead After 3 days | Std. dev | % Increase over Control |
|---|---|---|---|
| Control | 6238 | 688 | |
| TP508 30 nM | 7463 | 167 | 19.7 |
| TP508 300 nM | 8882 | 148 | 42.4 |
| TP508 3 μM | 8866 | 4 | 42.1 |
| TP508 30 μM | 7772 | 258 | 24.6 |

EXAMPLE 3B

NPAR Agonist Stimulation of Proteoglycan Synthesis in Cultured Rat Articular Chondrocytes To determine the effectos of the NPAR agonist TP508 on proteoglycan synthesis, 3-dimensional alginate cultures were prepared as described above and assayed for incorporation of [$^{35}S$]-sulfate. Bead cultures were exposed to indicated concentrations of TP508 as well as [$^{35}S$]-sulfate (20 μCi/ml) and with daily medium changes and were harvested on days 7 for [$^{35}S$]-sulfate incorporation. At each time point 5–10 beads were removed, washed 3× with 0.9% saline, dissolved by adding 0.5 ml of 55 mM sodium citrate, 0.15 M NaCl at 37 C for 10 minutes as described above, and counted in a liquid scintillation counter. [$^{35}S$]-sulfate incorporation was normalized in each sample for number of beads added. As shown in Table 3, TP508 treatment alone at a concentration of 300 nM (about 0.7 μg per ml), stimulated [$^{35}S$]-sulfate incorporation about 50% over controls. There was also a large stimulation by 30 μM TP508 (about 70 μg per ml), however, there was a large relative standard deviation in measurements at this concentration.

TABLE 3

Effect of the NPAR agonist TP508 on [$^{35}$S]-sulfate incorporation into proteoglycans.

| Treatment | CPM/bead | Std. dev | % Increase over Control |
|---|---|---|---|
| Control | 665 | 24 | |
| TP508 30 nM | 829 | 87 | 24.7 |
| TP508 300 nM | 1008 | 29 | 51.6 |
| TP508 3 µM | 827 | 9 | 24.1 |
| TP508 30 µM | 1153 | 519 | 73.3 |

EXAMPLE 4
Preparation of Polylactic Acid/Polyglycolic Acid Copolymer Microspheres of TP508

A double emulsion technique was used to prepare microspheres of polylactic acid/polyglycolic acid copolymer (PLGA) containing TP508. Briefly, the matrix components were dissolved in methylene chloride and TP508 was dissolved in water. The two were gradually mixed together while vortexing to form a water-in-oil (W/O) emulsion. Polyvinyl alcohol (0.3% in water) was added to the emulsion with further vortexing to form the second emulsion (O/W), thereby forming a double emulsion: an O/W emulsion comprised of PLGA droplets, and within those droplets, a second disperse phase consisting of TP508 in water. Upon phase separation, the PLGA droplets formed discrete microspheres containing cavities holding TP508. To cause phase separation of the microspheres, a 2% isopropyl alcohol solution was added. The particles were collected by centrifugation, and then lyophilized to remove residual moisture. The composition of the matrix was varied to form microspheres with different release kinetics (Table 4).

TABLE 4

Composition of different microsphere formulations

| Formulation | PLA:PGA | Polymer M. Wt. | % TP508 | % polyethylene glycol |
|---|---|---|---|---|
| A | 50:50 | 46,700 | 5 | 0 |
| B | 50:50 | 7,200 | 5 | 0 |
| C | 50:50 | 46,700 | 5 | 5 |
| D | 50:50 | 46,700 | 5 | 0 |
| E | 75:25 | 120,000 | 5 | 0 |

The mean diameter of the microspheres was measured in a Coulter counter and the drug entrapment efficiency was measured by spectrophotometric assay at 276 nm following dissolution of a weighed sample of microspheres in methylene chloride and extraction of the released drug into water (Table 5).

TABLE 5

Formulation diameter and drug entrapment efficiency

| Formulation | Diameter, µm | TP508 Entrapment, % |
|---|---|---|
| A | 26.0 | 53.8 |
| B | 16.2 | 27.1 |
| C | 17.6 | 58.9 |
| D | 23.9 | 42.6 |
| E | 25.8 | 36.2 |

To measure TP508 release from the different PLGA matrices, 20 mg of microspheres were placed in 1.0 ml of PBS contained in 1.5 ml polypropylene microcentrifuge tubes. Tubes were incubated at 37° C. and shaken at 60 rpm. At various times, the tubes were centrifuged and the supernatant containing released TP508 was removed and frozen for subsequent analysis. Fresh PBS was added to the microspheres and incubation was continued. TP508 in the supernatant was measured by absorbance at 276 nm. For each formulation, quadruplicate release determinations were performed. Formulations B and D showed no detectable drug release during 28 days of incubation at 37° C. The remaining formulations all released detectable amounts of TP508, although in all cases the amount of drug released fell below detectable limits (<1 µg/mg matrix/day) within 3–4 days. Formulations A and C showed the greatest release of TP508, releasing 60–80% of the entrapped drug over 3–4 days. Formulation C showed the fastest release kinetics and was chosen for testing in the rabbit cartilage defect model described in Example 5.

EXAMPLE 5
The NPAR Agonist TP508 Stimulates Cartilage Growth in Rabbit Models

Young, male New Zealand rabbits (2–3 kilograms) (n=15) were anesthetized and given bilateral, medial longitudinal parapatellar arthrotomies. The skin, subcutaneous tissue and joint capsule were incised, using electrocautery to minimize bleeding. The joint surface was exposed by lateral dislocation of the patella. A 3-mm diameter, 1–2-mm deep full-thickness defect was made in the trochlear groove of the femur using a surgical drill and pointed stainless steel drill bit. The aim was to extend the defect into the subchondral plate without piercing the subchondral bone.

The rabbits were divided into three groups. For each rabbit, both right and left trochlear groove defects were filled with the same treatment. For this study, TP508 was formulated into PLGA controlled release microspheres, prepared as described in Example 4 (Formulation C). The microspheres were mixed with sufficient Pluronic F68 gel (5% w/v) to bind the spheres together into a paste-like consistency that could easily be packed into the defect. The control group received PLGA microspheres without TP508 in both defects. The treated groups received microspheres containing either 10 or 50 mg of TP508/defect. One rabbit from each group was sacrificed at 4 weeks, 2 from each group were sacrificed at 6 weeks and the remaining animals were sacrificed at 9 weeks. Samples were fixed and processed for histological analysis.

At the time of sacrifice, there appeared to be considerable fibrous granulation tissue and no evidence of white cartilage-like material in the control defects. In contrast, the defect had a nearly uniform, dense, white material filling in the defects from the 10 µg treated group and 50 µg group. By 6 weeks post-surgery, the macroscopic differences between treated and control defects were not so pronounced.

Histology of the four week samples showed that indeed the control defects were filled with what appeared to represent early granulation tissue including inflammatory and fibroblastic cells. In contrast, the 10 and 50 microgram treated defects appeared to have a large number of chondrocytes and early signs of cartilage formation. This effect was seen more dramatically at week six. Controls had a small amount of connective tissue, yet little evidence of cartilage repair. In contrast, in both the 10 µg and 50 µg treated defects, there appeared to be good integration with hyaline cartilage forming at the top of the defect and extensive subchondral bone repair.

Nine-week TP508 treated defects exhibited a predominantly hyaline matrix with evidence of significant aggrecan content as shown by positive safranin-O staining. In most instances there was no difference in aggrecan content between the repair site and native tissue. Histological results were quantitatively assessed using a grading system adapted by Freed, et al., *J. Biomed. Materials Res.* 28:891–899 (1944) from the scheme of O'Driscoll, et al., *J. Bone Joint Surg.* 126:1448–1452 (2000) with a maximum score of 25 for normal articular cartilage. Experimental TP508 treated defects scored mean averages that were significantly higher than control defects (Table 6).

TABLE 6

Histology Scoring For Articular Defect Study

| Milligrams of TP508 | Repair Score ± SE |
|---|---|
| 0 | 9.4 ± 1.6 |
| 10 | 18.6 ± 1.4 |
| 50 | 19.8 ± 1.0 |

Peptide treated defects repaired with smooth articular surfaces and were typically well bonded at the junction between repair and native tissue. The quality of control repair tissue was characterized as mostly fibrocartilage with poor quality joint surfaces. Integration at the junction between repair and native tissue was usually poor. Overall, the quality of cartilage repaired with TP508 was significantly enhanced over control non-treated defects. This improved quality of repair tissue should lead to more durable and functional restoration of joint biomechanics and reduction in the incidence of osteoarthritis in patients suffering from traumatic cartilage injuries.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of stimulating cartilage growth or repair at a site in a subject in need of such growth or repair, said method comprising the step of administering to the site a therapeutically effective amount of an agonist of the non-proteolytically activated thrombin receptor, wherein the agonist comprises a peptide represented by the following structural formula:

Asp-Ala-R, wherein R is a serine esterase conserved sequence.

2. The method of claim 1 wherein the site is an arthritic joint.

3. The method of claim 1 wherein the site is being treated for cartilage damage or loss.

4. The method of claim 1 wherein the site is being treated for cartilage damage or loss due to traumatic injury.

5. The method of claim 1, wherein the agonist is a peptide of between 12 and about 23 amino acids.

6. The method of claim 5, wherein the peptide comprises a C-terminal amide.

7. The method of claim 6, wherein the serine esterase conserved sequence comprises the amino acid sequence of SEQ ID NO: 1 (Cys-Glu-Gly-Asp-Ser-Gly-Gly-Pro-Phe-Val), or a C-terminal truncated fragment thereof consisting of at least nine amino acids, provided that zero, one or two of the amino acids in the serine esterase conserved region are conservative substitutions of the corresponding amino acid in SEQ ID NO: 1.

8. The method of claim 6, wherein the serine esterase conserved sequence comprises the amino acid sequence of SEQ ID NO: 2 (Cys-$X_1$-Gly-Asp-Ser-Gly-Gly-Pro-$X_2$-Val), wherein $X_1$ is Glu or Gln and $X_2$ is Phe, Met, Leu, His or Val, or a C-terminus truncated fragment of SEQ ID NO: 2, said fragment consisting of least six amino acids.

9. The method of claim 8, wherein the peptide comprises the amino acid sequence Arg-Gly-Asp-Ala (SEQ ID NO: 3).

10. The method of claim 9, wherein the peptide comprises the amino acid sequence Arg-Gly-Asp-Ala-Cys-$X_1$-Gly- Asp-Ser-Gly-Gly-Pro-$X_2$-Val (SEQ ID NO: 4), wherein $X_1$ is Glu or Gln and $X_2$ is Phe, Met, Leu, His or Val.

11. The method of claim 6, wherein the peptide comprises the amino acid sequence Ala-Gly-Tyr-Lys-Pro-Asp-Glu-Gly-Lys-Arg-Gly-Asp-Ala-Cys-Glu-Gly-Asp-Ser-Gly-Pro-Phe-Val (SEQ ID NO: 6), or is an N-terminal truncated fragment thereof, provided that zero, one, two or three amino acids at positions 1–9 in the agonist are conservative substitutions of the amino acid at the corresponding position of SEQ ID NO: 6.

12. The method of claim 11, wherein the peptide is administered in a pharmaceutical composition additionally comprising an implantable, biocompatible carrier.

13. The method of claim 12, wherein the carrier comprises a polylactic acid homopolymer, polyglycolic homopolymer or copolymer.

14. The method of claim 6, wherein the peptide comprises the amino acid sequence Ala-Gly-Tyr-Lys-Pro-Asp-Glu-Gly-Lys-Arg-Gly-Asp-Ala-Cys-Glu-Gly-Asp-Ser-Glv-Gly-Pro-Phe-Val (SEQ ID NO: 5), or an N-terminal truncated fragment thereof.

15. A method of stimulating cartilage growth or repair at a site in a subject in need there such growth or repair, said method comprising the step of administering to the site a therapeutically effective amount of a peptide of 23 amino acids comprising the sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 6).

16. A method of stimulating cartilage growth at an arthritic joint in a subject, said method comprising the step of administering to the site a therapeutically effective amount of a C-terminus amidated peptide of 23 amino acids comprising the sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 6).

17. A method of stimulating cartilage growth in a subject at a site being treated for cartilage loss, said method comprising the step of administering to the site a therapeutically effective amount of a C-terminus amidated peptide of 23 amino acids comprising the sequence Ala-Gly-Tyr-Lys-Pro-Asp-Glu-Gly-Lys-Arg-Gly-Asp-Ala-Cys-Glu-Gly-Asp-Ser-Gly-Glv-Pro-Phe-Val (SEQ ID NO: 6).

18. A method of stimulating cartilage growth in a subject at a site being treated for cartilage loss due to traumatic injury, said method comprising the step of administering to the site a therapeutically effective amount of a C-terminus amidated peptide of 23 amino acids comprising the sequence Ala-Gly-Tyr-Lys-Pro-Asp-Glu-Gly-Lys-Arg-Gly-Asp-Ala-Cys-Glu-Gly-Asp-Ser-Glv-Gly-Pro-Phe-Val (SEQ ID NO: 6).

19. A method for culturing chondrocytes in vitro, the improvement comprising culturing the chondrocytes in the presence of a stimulating amount of an NPAR agonist.

20. The method of claim 19, further comprising the step of administering a therapeutically effective amount of the cultured chondrocytes to a site in a subject in need of cartilage repair or growth.

21. The method of claim 5, wherein the peptide is unsubstituted at the C-terminus.

* * * * *

UNITED STATES PATENT AND TRADEMARK OFFICE
CERTIFICATE OF CORRECTION

PATENT NO. : 6,815,416 B2
DATED : November 9, 2004
INVENTOR(S) : Darrell H. Carney et al.

It is certified that error appears in the above-identified patent and that said Letters Patent is hereby corrected as shown below:

Column 17,
Line 5, insert -- Gly -- before "Pro";
Line 7, insert -- or -- before "two";
Line 7, delete "or three";
Line 19, delete "Glv" and insert -- Gly --;
Line 20, delete "5" and insert -- 6 --;
Line 20, insert -- is -- before "an"
Line 23, delete "there" and insert -- thereof --;
Line 25, insert -- C-terminus amidate -- before "peptide".

Column 18,
Lines 11 and 18, delete "Glv" and insert -- Gly --.

Signed and Sealed this

First Day of March, 2005

JON W. DUDAS
*Director of the United States Patent and Trademark Office*